(12) United States Patent
Tamura et al.

(10) Patent No.: US 6,651,538 B2
(45) Date of Patent: Nov. 25, 2003

(54) MICROTOME

(75) Inventors: Isao Tamura, Kyoto (JP); Sumio Nakajima, Kyoto (JP)

(73) Assignee: Dosaka EM Co., Ltd., Kyoto (JP)

( * ) Notice: Subject to any disclaimer, the term of this patent is extended or adjusted under 35 U.S.C. 154(b) by 0 days.

(21) Appl. No.: 10/303,387

(22) Filed: Nov. 25, 2002

(65) Prior Publication Data

US 2003/0101858 A1 Jun. 5, 2003

(30) Foreign Application Priority Data

Nov. 30, 2001 (JP) ........................................ 2001-366009

(51) Int. Cl.[7] ................................................ B26D 5/08
(52) U.S. Cl. .......................... 83/575; 83/915.5; 83/577; 83/956; 83/647; 606/169
(58) Field of Search ................................. 83/915.5, 575, 83/577, 956, 647, 491; 606/169, 171; 335/276

(56) References Cited

U.S. PATENT DOCUMENTS

| | | | | |
|---|---|---|---|---|
| 3,599,523 A | * | 8/1971 | Pickett | 83/412 |
| 4,024,779 A | * | 5/1977 | Taugner et al. | 83/165 |
| 4,126,069 A | * | 11/1978 | Shimonaka | 83/703 |
| 4,967,629 A | * | 11/1990 | Behme | 83/714 |
| 5,282,404 A | * | 2/1994 | Leighton et al. | 83/13 |
| 5,535,654 A | * | 7/1996 | Niesporek et al. | 83/364 |
| 5,713,255 A | * | 2/1998 | Izvozichikov et al. | 83/24 |
| 5,752,425 A | * | 5/1998 | Asakura et al. | 83/713 |
| 5,906,148 A | * | 5/1999 | Aihara et al. | 83/72 |

* cited by examiner

*Primary Examiner*—Allan N. Shoap
*Assistant Examiner*—P Hong Nguyen (57) ABSTRACT

Disclosed is an apparatus for cutting a specimen with a blade that moves forward with oscillation. The apparatus is free from vertical wobbling of the blade even after a long period of use, so that the cutting is carried out without killing cells present in the specimen. The blade is attached to a movable body that is coupled to a base with a resilient coupler. The base is provided with a driving electromagnet, and the movable body is provided with a permanent magnet. Thus, the movable body oscillates by supplying a control signal to the driving electromagnet.

17 Claims, 9 Drawing Sheets

MICROTOME

BACKGROUND OF THE INVENTION (1) Field of the Invention

The present invention relates to a microtome for cutting e.g. a brain specimen into thin slices for use in physiological experiments.

(2) Description of the Related Art

One example of a conventional microtome is disclosed in Publication of Examined Japanese Patent Application No. SHO 58(1983)-29453. The microtome disclosed therein has a stage onto which a specimen is fixedly placed and a base driven by a motor to slide relatively to the stage. The base is provided with a movable body that oscillates in a direction perpendicular (side-to-side direction) to the sliding direction. The movable body is provided with a cutting blade attached thereto, and with another motor mounted on the base. The rotational movements produced by said another motor are converted by a crank mechanism into horizontal movements to oscillate the movable body, i.e. the cutting blade in the horizontal direction. Wile oscillating, the cutting blade is moved forward by the slide thereby cutting a thin slice from the specimen.

A conventional microtome as above works well while it is new, but eventually causes a problem with a dovetailed recess provided in the base that is in fit with a dovetail tenon protruded from the movable body. To be more specific, through the use over a long period of time, the dovetailed recess wears out, thereby producing an undesirable play. Due to the play, the fit between a rotation shaft and a coupler constituting the crank mechanism becomes poor. Such poor fit causes the cutting blade to wobble horizontally (oscillation in the horizontal direction) As a result, the cutting blade ends up smashing the specimen from above thereby killing cells present in the specimen. This is a problem especially in brain physiology experiments as whether cells in a specimen used are dead or alive greatly matters in the study.

In view of the above problems, an object of the present invention is to provide a microtome that is free from horizontal wobbling of a cutting blade even after a long period of use, so that thin slices of a specimen are obtained in good condition with the cells remain alive.

Another object of the present invention is to provide a microtome capable of oscillating only in a desired direction while suppressing oscillation in other directions.

Yet another object of the present invention is to provide a microtome of which cutting blade oscillates to achieve sharp cutting, i.e., swings quickly from side to side making a click-like motion between each swing.

Yet another object of the present invention is to provide a microtome capable of suppressing the judder that may occur at a mechanical resonance when the oscillation frequency is made to vary.

Yet another object of the present invention is to provide a microtome of which oscillation amplitude and frequency are adjustable, so that a specimen is optimally cut depending on the type or the state of the specimen.

SUMMARY OF THE INVENTION

To achieve the above stated objects, a microtome according to the present invention includes: a stage for fixedly placing the specimen thereon; a base arranged slidably relative to the stage; a movable body arranged to oscillate in a direction perpendicular to a direction in which the base slides; a cutting blade for cutting the specimen placed on the stage, the cutting blade being attached to the movable body at a forward part with respect to the sliding direction; a plurality of resilient couplers coupling the movable body to the base so as to allow for the oscillation; a first magnet made of an electromagnet and mounted on one of the base and the movable body; a control circuit for supplying an alternating signal to the first magnet; and a second magnet mounted on the other of the base and the movable body in opposed relation to the first magnet. The second magnet reacts to attraction and repulsion that is alternately resulting from an alternating field generated by the first magnet, so that the movable body is displaced against resilience of the resilient couplers in the direction perpendicular to the sliding direction, whereby the cutting blade oscillates. By sliding the base forward relative to the stage, the cutting blade cuts into the specimen with oscillation so that the thin slice is cut from the specimen.

Here, the plurality of resilient couplers maybe arranged in a pair. Each resilient coupler may be made up of a plurality of spring plates overlapped in layers. The pair of resilient couplers may be attached to the base with a first end of each resilient coupler being fixed to the base at two separate locations, and a second end of each resilient coupler being fixed to the movable body at lateral sides.

Here, the second magnet may be a permanent magnet. The second magnet may be different from the first magnet in magnetic pole distance. The first magnet may generate, when energized, magnetic force attracting the second magnet in a direction where unlike polarities are adjacent to each other owing to the different magnetic pole distance.

Further, the first magnet may be fixed to the base. The second magnet may be made of a permanent magnet magnetized to have a north pole and a south pole at respective ends thereof. The permanent magnet may be fixed to the movable body with the north pole and the south pole opposing to a pair of legs of a core of the first magnet.

Here, the microtome may further include: a detector for detecting a magnitude of a current passing through the first magnet; and a current control circuit for controlling the current passing through the first magnet so that the detector detects a constant magnitude.

Here, the microtome may further include an operating unit for variably controlling an amplitude and a frequency of the current passing through the first magnet.

With the above construction, the microtome includes the cutting blade for slicing a specimen, and the cutting blade is attached to the movable body that is coupled to the base with the resilient couplers. The blade is made to oscillate through the use of the driving electromagnet and the magnet on the principles of a linear motor. Thus, the microtome operates without deterioration even after a long period of use, and is capable of cutting the specimen without killing the cells present in the specimen. Further, since the blade oscillates with the use of the electromagnet and the magnet in combination, the movable body oscillates more powerfully.

Still further, since each resilient coupler is made of a plurality of spring plates overlapped in layers, the movable body is allowed to oscillate only in the fixed direction.

Still further, the permanent magnet mounted on the movable body is magnetized in the thickness direction, so that each side of the magnet has unlike polarity from each other. This arrangement helps the movable body to oscillate more powerfully. Consequently, the blade cuts a specimen more sharply.

Still further, the presence of feedback circuit serves to suppress the judder that may occur at mechanical resonance when the oscillation frequency is made to vary.

Still further, since the frequency and the amplitude of oscillation of the blade is variable in a continuous manner, adjustment maybe made to achieve an optimal cutting of a specimen depending on the stiffness or other properties of the specimen.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings.

DESCRIPTION OF THE PREFERRED EMBODIMENT

Hereinafter, description is given to embodiments of the present invention with reference to the accompanying drawings.

Figure 1:
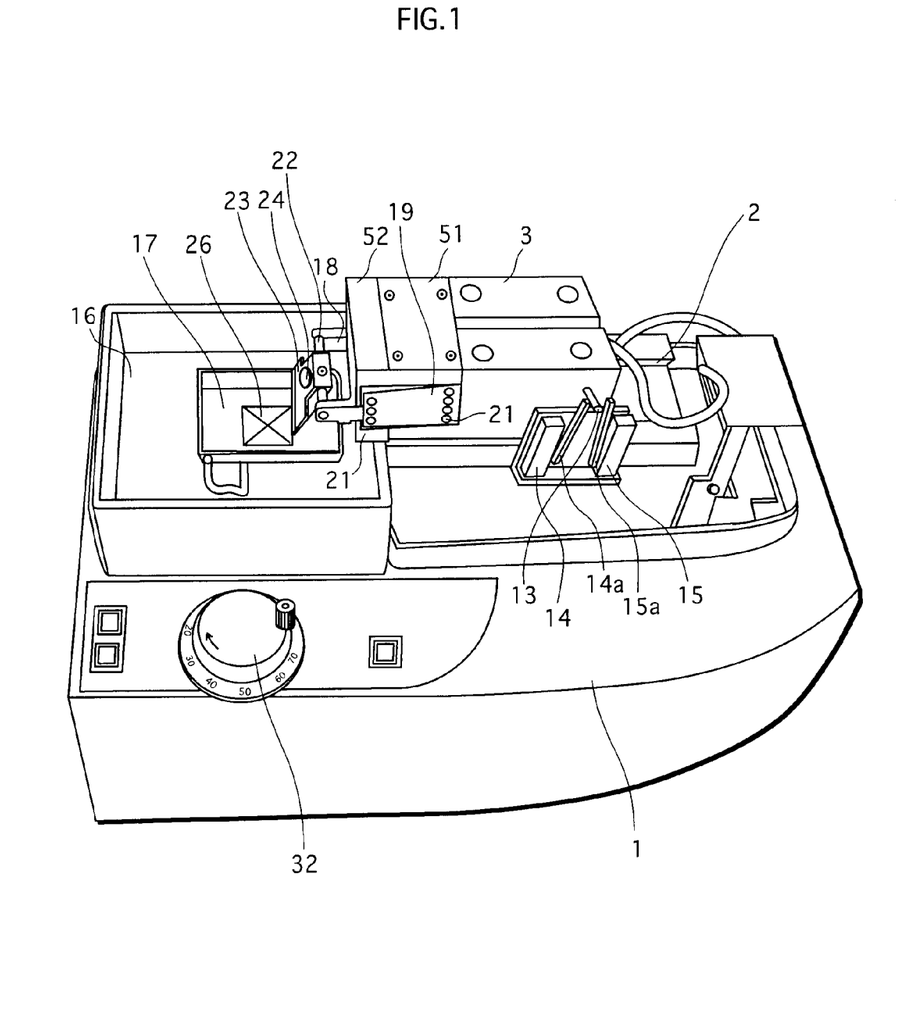
FIG. 1 is an oblique view showing a microtome according to an embodiment of the present invention.
Figure 2:
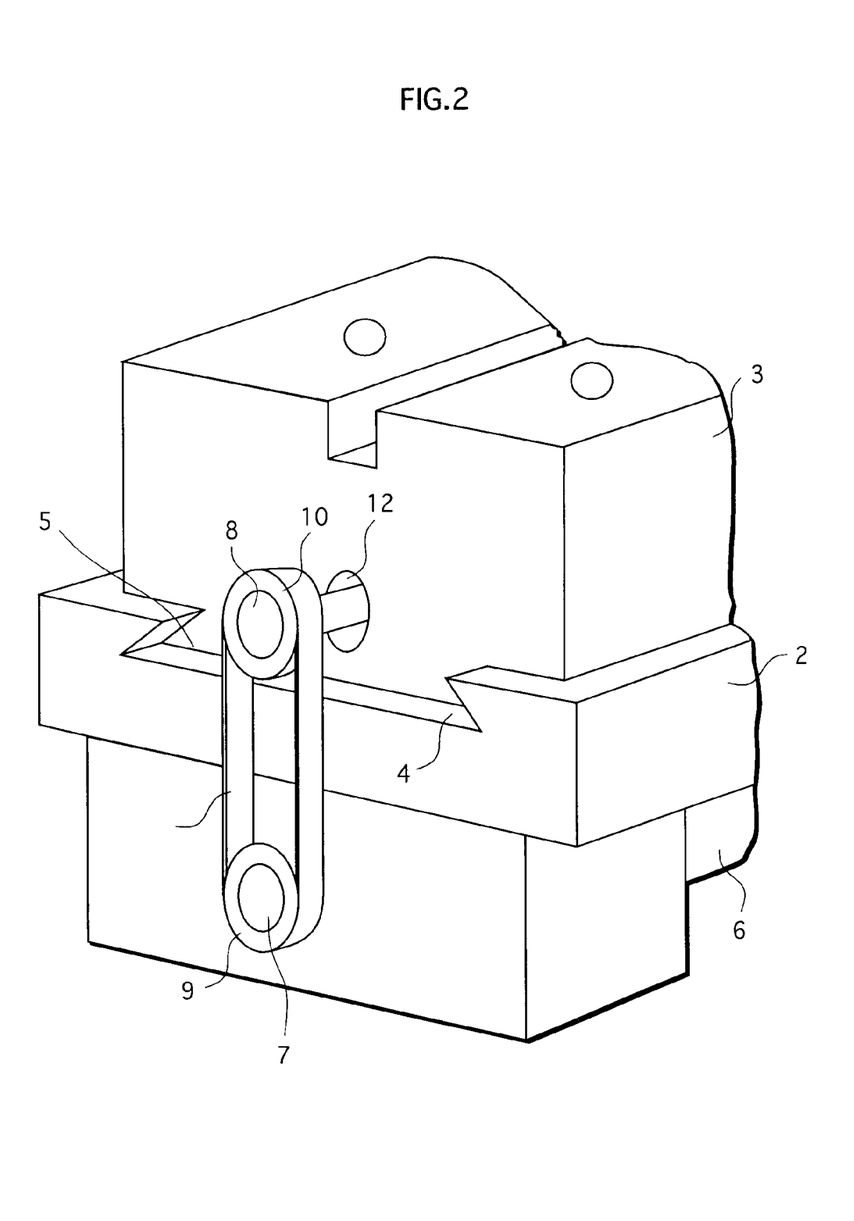
FIG. 2 is an oblique view showing a part of the microtome shown in FIG. 1.

As shown in FIG. 1, a table 2 is mounted on a main body 1, and a base 3 is slidably mounted on the table 2. To construct the sliding mechanism, the table 2 has, as shown in FIG. 2, a dovetailed recess 4, and the base 3 has a dovetail tenon 5. The dovetail tenon 5 fits into the dovetailed recess 4 so that the base 3 slides over the table 2. Pulleys 9 and 10 are respectively arranged around a rotation shaft 7 of a gear motor 6 and a rotation shaft 8 inserted in a bore 12 that is formed through the base 3. The two pulleys are belt-engaged with a belt 11, so that rotational movement of the gear motor 6 is transmitted to the rotation shaft 8 via the belt 11. The rotation shaft 8 is inserted deep into the bore 12 in the base 3, and has threads for engagement with a thread formed on the wall surface of the bore 12. With this construction, the base 3 slides in one direction by driving the gear motor 6. By driving the gear motor 6 in the reverse direction, the base 3 slides in the opposite direction.

Referring now back to FIG. 1, a protuberance 13 extending from the base 3 is located between movable pieces 14a and 15a of switches 14 and 15, respectively. When the base 3 moves forward a predetermined distance, the protuberance 13 comes to press the movable piece 14a thereby activating the switch 14. As a result, the gear motor 6 operates in the reverse direction to move the base 3 backward. When the base 3 moves backward for a predetermined distance, the protuberance 13 now comes to press the movable piece 15a thereby activating the switch 15. As a result, the base 3 comes to a halt.

As shown in FIG. 1, the main body 1 is provided with a casing 16 at the front of the table 2 (hereinafter, the left hand side in FIG. 1 is referred to as the front, and the right hand side is referred to as the back). Provided inside the casing 16 is a tray 17 for placing a specimen thereon. The detailed description is given later.

Figure 3:
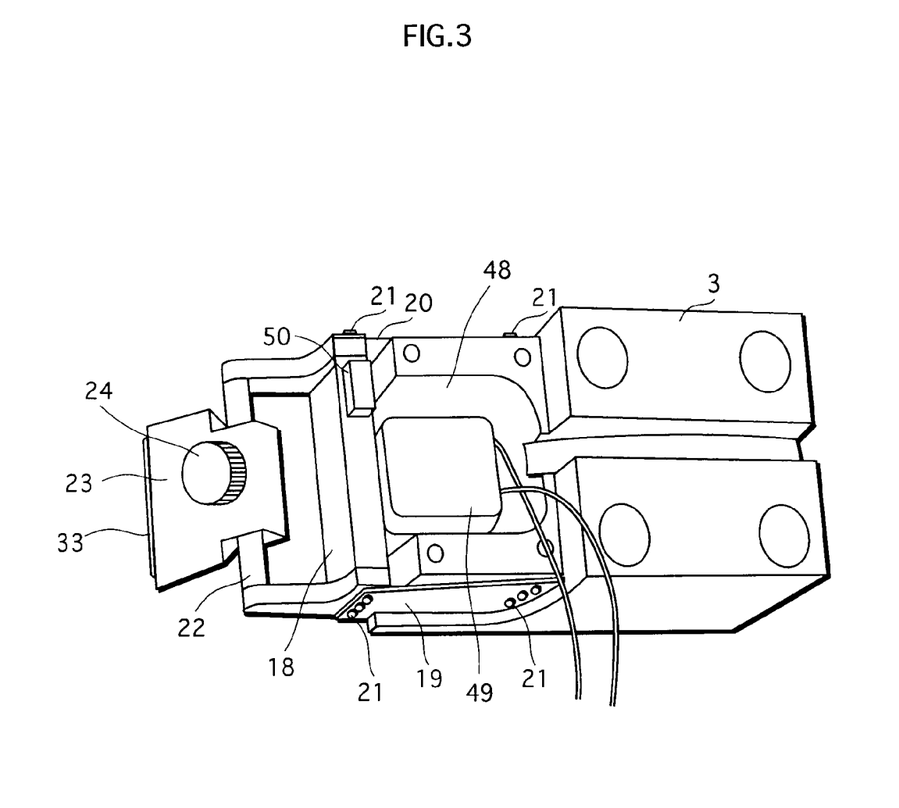
FIG. 3 is an oblique view showing a part of the microtome.
Figure 4:
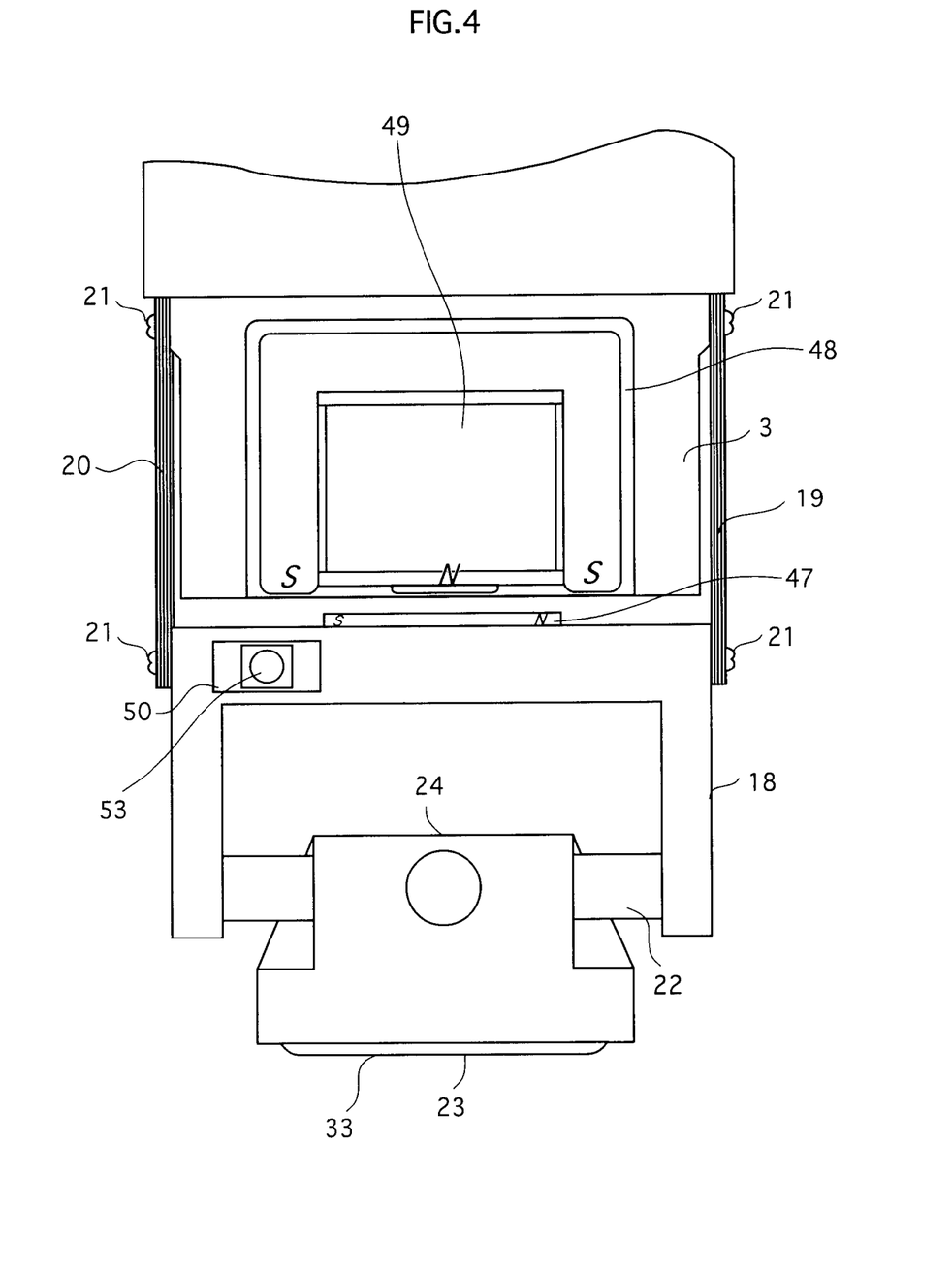
FIG. 4 is a plan view showing a part of the microtome.

The base 3 is provided with a movable body 18 at the front. To be more specific, the movable body 18 is coupled to the base 3 with resilient couplers 19 and 20 at their lateral sides. FIGS. 3 and 4 more clearly show the coupling. As most clearly shown in FIG. 4, each of the resilient couplers 19 and 20 is constructed by laminating in layers four or so spring plates (thickness of the order of 0.5–0.2 mm) each made of e.g. stainless steel. Each set of the spring plates is firmly fixed to the base 3 at one end and to the movable body 18 at the other end using bolts 21, so that the spring plates stand vertical.

Preferably, the resilient couplers 19 and 20 have resilience in the horizontal direction but no resilience in the vertical direction, and free from a twist. In order to eliminate such a twist, the spring plates are more preferably of a shorter length, e.g. 40 mm or so. With such arrangement, the movable body 18 substantially moves only in the side-to-side direction relative to the base 3.

The movable body 18 is provided with a mounting bar 22. Rotatably mounted on the mounting bar 22 is a support 23 for supporting a cutting blade with which the specimen is cut. For secure attachment of the support 23 to the movable body 18, a screw 24 is in engagement with the mounting bar 22. To attach a cutting blade (hereinafter, simply referred to as a "blade") 33, the screw 24 is loosen to allow for rotation of the support 23 to a position for easy mounting of the blade 33. Through an adjustment implemented by the screw 24, the blade 33 is set precisely in a desired direction (horizontal direction) relative to a specimen 25.

As shown in FIGS. 1, 3 and 4, the overall configuration of the microtome is bilaterally symmetric, especially in parts that contribute to oscillation, such as the base 3, the movable body 18, and the resilient couplers 19 and 20. In addition, the resilient couplers 19 and 20 are precisely configured to allow for side-to-side oscillation only. Thus, the movable body 18 is free from any undesirable oscillation.

Figure 5:
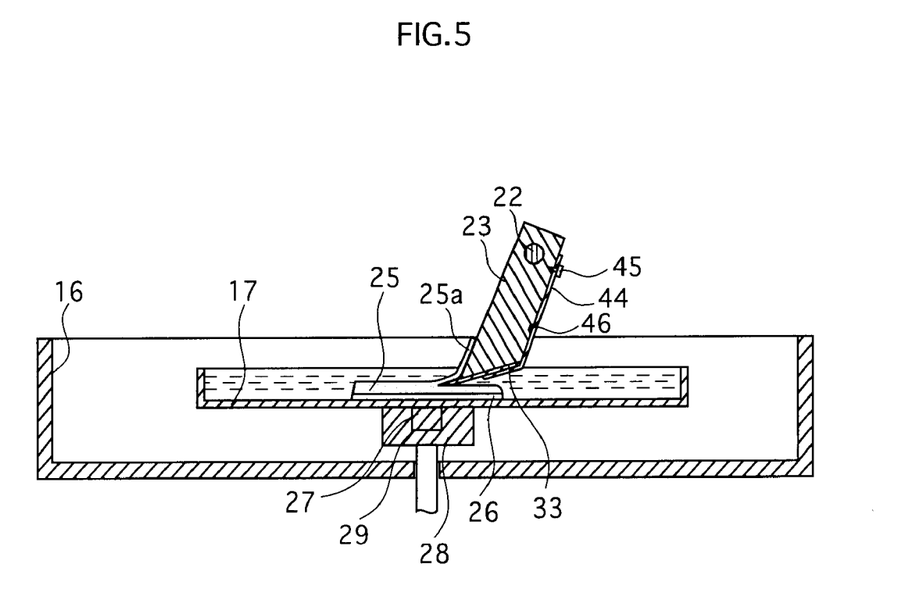
FIG. 5 is a sectional view showing apart of the microtome.
Figure 6:
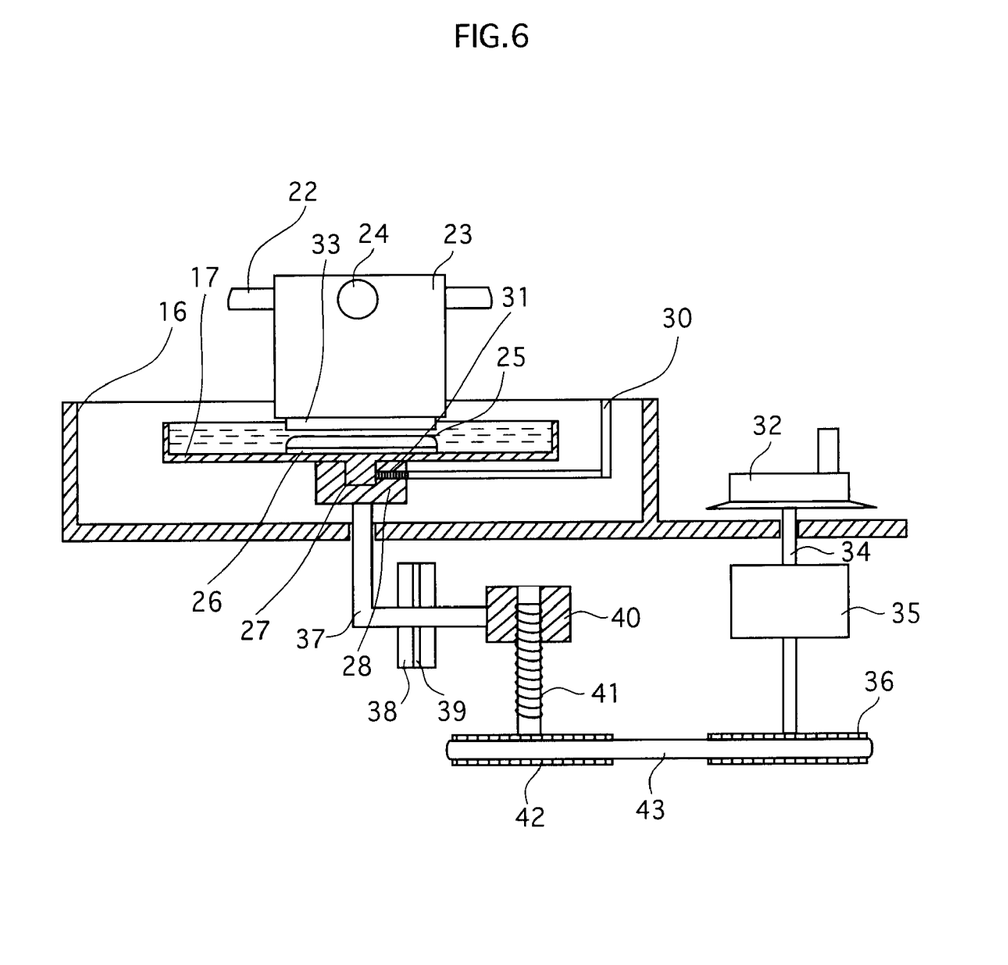
FIG. 6 is a sectional view showing a part of the microtome.

Next, referring to FIGS. 5 and 6, description is given to the tray 17 and the blade for slicing the specimen. Provided in the center of the tray 17 is a specimen stage 26 on which the specimen 25 is placed. The specimen stage 26 is to ensure positioning of the specimen, and may be omitted. On the undersurface thereof, the tray 17 has a projection 27 that fits within a hole 29 formed in a support bed 28. The tray 17 is fixed to the support bed 28 with a screw 31 that is coupled to a lever 30. The lever 30 is to operate the screw 31 from above the casing 16.

The support bed 28 is moved up and down by rotating a knob 32 that is exposed from the upper surface of the main body 1. With the use of the knob 32, the tray 17 is moved up and down so that the position of the specimen 25 is adjusted relative to the blade 33 that is attached to a lower end of the support 23.

FIG. 6 shows a mechanism of cooperation between the knob 32 and the support bed 28. A stepping motor 35 is coupled to a rotation shaft 34 of the knob 32, and a pulley 36 is attached to the motor 35. Extending from the under surface of the support bed 28 is a coupling bar 37 having a projection (not illustrated) that fits into a groove 39 formed in the sliding mechanism 38. Further, the coupling bar 37 has a female screw 40 attached at the end. The female screw 40 engages a male screw 41 around which a pulley 42 is mounted. The two pulleys 36 and 42 are belt-engaged by a belt 43. Description is given later to the operations of this mechanism.

Now, description is given to means to attach the blade 33. As shown in FIG. 5, attached to the support 23 along its back and bottom surface is a fixing plate 44 that is made of stainless steel and that has an L-shaped cross section. The fixing plate 44 is fixed to the support 23 with a screw 45 at an upper part of the back surface of the support 23. In addition, a lower part of the fixing plate 44 is inwardly pulled and pressed against the lower part of the support 23 due to the spring tension of the fixing plate 44. The support 23 has a cavity 46 formed in the back surface. To attach the blade 33, a stick-like member is inserted into the cavity 46 to lift the fixing plate 44 away from the support 23 so as to provide a clearance between the fixing plate 44 and the support 23 at their lower portions. In this state, the blade 33 is inserted into the clearance and the stick-like member is then removed. As a result, the blade 33 is firmly attached to the support 23.

The blade 33 may be a commercially available razor blade. Especially suitable is a two-edged razor blade that is broken into halves i.e., two one-edged blades. The blade 33 is fixed to the support 23 in a manner that the blade 33 inclines at an angle of about 15° to the upper surface of the specimen stage 26 placed on the tray 17. With this arrangement, the lower edge of the blade 33 (the portion actually cuts the specimen) is made parallel to the specimen stage 26. In addition, the lower edge of the fixing plate 44 stays out of contact with the specimen 25, so that the fixing plate 44 does not damage the specimen 25.

Now, with reference to FIGS. 3 and 4, description is given to the mechanism for oscillating the movable body 18. The movable body 18 has on the back surface thereof an I-shaped permanent magnet 47 that is fixed horizontally so as to be bilaterally symmetric. Preferably, the permanent magnet 47 is neodymium. Opposing to the permanent magnet 47, a driving electromagnet 49 is fixedly fit in a front-concavity 48 of the base 3. The driving electromagnet 49 is composed of an E-shaped core 54 and a coil 55 wound around a middle leg of the E-shaped core. The distance between the right leg and left leg of the E-shaped core 54 (the distance between the south pole and the north pole) differs from the distance between the south pole and the north pole of the permanent magnet 47.

The movable body 18 has another permanent magnet 50 fixed on the upper surface. The front-concavity 48 of the base 3 that is in opposing relation to the permanent magnet 50 is covered by a cover plate 52 on the front and a cover plate 51 next to the cover plate 52. There is provided a sensor coil 53 fixed on the rear surface of the cover plate 52. With this arrangement, the sensor coil 53 detects the oscillation amplitude of the movable body 18.

The permanent magnet 47 may simply be a bar magnet having the north pole and the south pole at the respective ends. However, more suitable is a single piece of solid object that is magnetized in the thickness direction so that the left half and the right half of the single piece facing to the driving electromagnet 49 each has unlike polarity from the other. Such an electromagnet magnetized in the thickness direction causes the blade 33 to oscillate more powerfully in a click-like motion, i.e., to swing at a faster speed. Consequently, the blade 33 manages to cut the specimen 25 sharply. Such a permanent magnet may be made of a single piece magnetized with the use of a specific magnetization technique. Alternatively, the permanent magnet may be made of a pair of magnets each magnetized in the thickness direction. In this case, each magnet is oriented, so that unlike polarities are aligned next to each other. Such a permanent magnet may have a different polarity from the other at each half separated in the middle without a gap, or it may be two pieces of magnets positioned side by side with a gap therebetween.

Figure 7A:
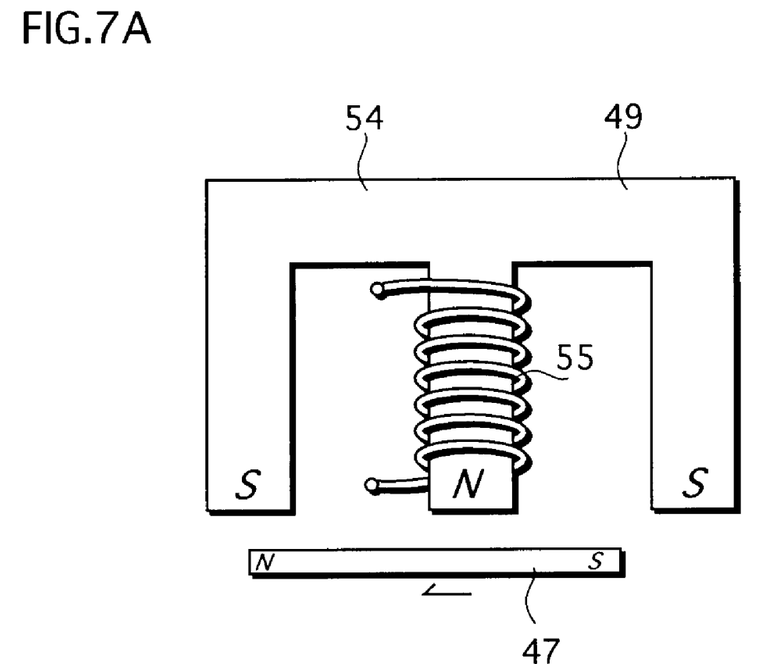
FIG. 7A is view showing the operational principle of a driving mechanism of the microtome.
Figure 7B:
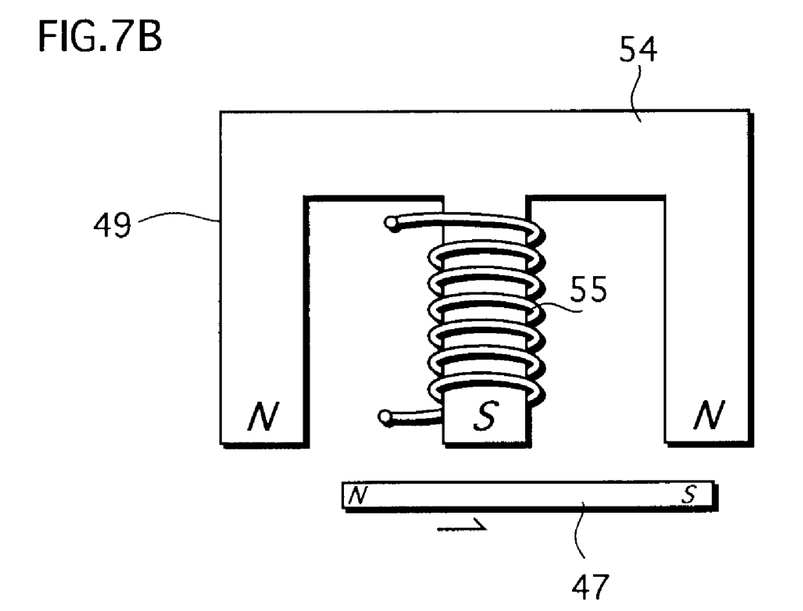
FIG. 7B is view showing the operational principle of the driving mechanism of the microtome.

As shown in FIG. 7, a control signal having a sine wave is supplied to the coil 55 that is wound around the middle leg of the E-shaped core 54. As shown in FIG. 7A, when the right and left legs of the E-shaped core 54 are magnetized to have the south polarity, while the middle leg is magnetized to have the north polarity, the permanent magnet 47 moves leftward. As shown in FIG. 7B, on the other hand, when the right and left legs of the E-shaped core 54 are magnetized to have the north polarity, and while the middle leg is magnetized to have the south polarity, the permanent magnet 47 moves rightward. The above operations are repeated to oscillate the movable body 18, i.e. the blade 33.

Figure 8:
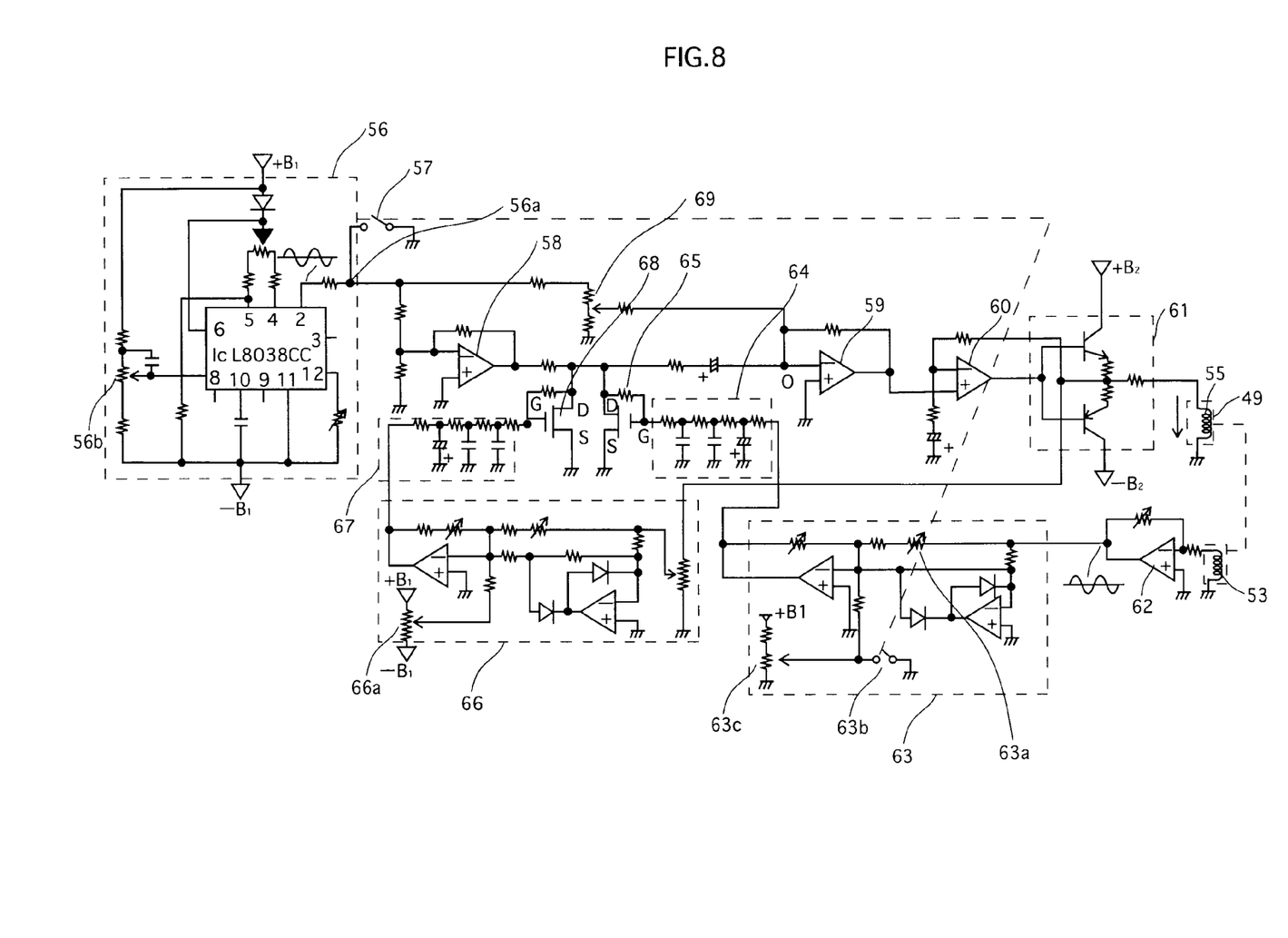
FIG. 8 is a schematic circuit diagram showing a driving circuitry of the microtome.

Next, with reference to FIG. 8, description is given to the driving circuitry for driving the microtome. There is provided a sing-wave generating circuit 56 of which output terminal 56a is earthed via a switch 57. A sign wave outputted from the output terminal 56a is supplied to a driving amplifier 60 via buffer amplifiers 58 and 59. An output of the driving amplifier 60 is supplied to an output amplifier 61 for amplification. An output of the output amplifier is then supplied to the coil 55 of the electromagnet 49. The sing-wave generating circuit 56 is provided with a variable resistor 56b for adjustment of the frequency of oscillation to be outputted.

The amplitude of the current passing though the coil 55 is detected by the sensor coil 53. An output of the sensor coil 53 is amplified in an amplifier 62 followed by full-wave rectification by a full-wave rectifier circuit 63. A variable resistor 63a is provided for full-wave rectifying peaks of the waves to be outputted from the full-wave rectifier circuit 63. Further, there is provided a switch 63b that operates in conjunction with the switch 57. When the switch 63b is on, the output terminal of the full-wave rectifier circuit 63 produces output at the maximum voltage. Further, there is provided a variable resistor 63c for adjusting the output voltage of the full-wave rectifier circuit 63.

The output of the full-wave rectifier circuit 63 is smoothed by a smoothing circuit 64 to be converted to dc voltage. The dc voltage is then applied to a gate electrode of an FET (field-effect transistor) 65 provided between the output terminal of the buffer amplifier 58 and the earth.

An output from the output amplifier 61 is supplied to a full-wave rectifier circuit 66 for full-wave rectification, and then to a smoothing circuit 67 for conversion into a direct current. The resulting output is then supplied to a gate electrode of an FET 68 provided between the output terminal of the buffer amplifier 58 and the earth. The full-wave rectifier circuit 66 is provided with a variable resistor 66a for adjusting the output voltage of the full-wave rectification. The components denoted by 66, 67, and 68 constitute a limiter.

Next, description is given to operations of the microtome constructed as above.

First, the blade 33 is attached to the support 23, and then the specimen 25 is placed and fixed with an instantaneous adhesive agent onto the specimen stage 26 on the tray 17. Here, the specimen 25 is a piece of a live organ (with live cells), such as liver, kidney, brain, or the like, of a mouse for example. The specimen 25 is of about 2–3 cm square and 1 cm or less in thickness. Next, the tray 17 is filled with a buffer solution (a solution for maintaining the cells in the same condition as they are present in a body) suitable to each organ until the specimen is completely covered. The buffer solution lubricates the blade 33 at the time of cutting the specimen 25. The casing 16 needs to be filled with ice in order to cool the specimen 25.

When the above preparation is done, a switch (not illustrated) is tuned on to move the base 3 forward. The base 3 is made to halt when the blade 33 comes above the tray 17 but before reaching to the specimen 25. In this state, the knob 32 is rotated to elevate the tray 17 to a level at which the blade 33 will cut the specimen 25.

Then, the switch is turned back on to move the blade 33 forward with oscillation, so that a thin slice is cut from the specimen 25. Upon completion of the cutting operation, the switch 14 is activated to reversely move the base 3. In conjunction with the reverse movement of the base 3, the stepping motor 35 is activated to move down the tray 17 by about 120 µm. Thereafter, the switch 15 is activated to stop the base 3. Successively, the stepping motor 35 is activated again to elevate the tray 17 back to the level set by the rotation of the knob 32.

If the base 3 is moved backward without lowering the tray 17, the blade 33 ends up damaging a newly cut surface of the specimen 25. Note that a thin slice 25a of the specimen 25 that is first cut is to be abandoned because the thin slice 25a may not be of a predetermined thickness.

Next, the knob 32 is rotated two full turns to elevate the tray 17 by about 200 µm, and thus the specimen 25 is elevated to the same extent. With this state, the cutting operation is performed so that a thin slice 25a of about 200 µm in thickness is cut from the specimen 25. As shown in FIG. 5, the thin slice 25a is moves along the front surface of the support 23 as it is cut from the specimen 25. As above, the operating means implemented by the knob 32 having a memory dial divided by tick marks enables thickness setting of the specimen slice by adjusting an amount of up-and-down movement of the specimen stage to be made for one forwarding movement of the base.

For shaper cutting, it is preferable that the side-to-side oscillation of the blade 33 is within the amplitude of about 1–2 mm. The oscillation frequency is adjusted according to the toughness or other property of the specimen 25. Generally, the frequency is within the range of 40–10 Hz, and a higher frequency is more preferable.

The movable body 18 is oscillated through the use of the driving electromagnet 49 and the permanent magnet 47 on the principles of a linear motor. Owing to this construction, the microtome is capable of performing the oscillation precisely as initially set even after a long period of use, and is free from undesired oscillation such as vertical wobbling as well as noise. Further, the resilient couplers 19 and 20 that couple the base 3 to the movable body 18 are precisely constructed to prevent vertical wobbling or twisting. Still further, the microtome is substantially bilaterally symmetric, so that the movable body 18, i.e., the blade 33, oscillates more smoothly without vertical wobbling and/or noise.

In addition, the base 3 and the movable body 18 are coupled to each other without using mechanical coupling such as a crank mechanism. This non-contact coupling eliminates the possibility of undesirable oscillation, such as vertical wobbling, even after a long period of use. That is, since the blade 33 is kept from vertical wobbling, there is no possibility that the blade 33 smashes the specimen 25 from above to kill the cells. Especially in physiological experiments, it greatly matters whether the cells present in the specimen slice 25a used are alive or not. With the microtome of this embodiment, the thin slice 25a is cut from the specimen 25 in good condition without killing the cells.

Now, with reference to FIG. 8, description is given to control operations of the microtome.

The variable resistor 56b makes it possible to continuously vary the oscillation frequency of the blade 33, and the variable resistor 63c makes it possible to continuously vary the oscillation amplitude. The variable resistors other than the above two are preset at a suitable value. For example, in the case where the variable resistor 63c is earthed, the variable resistor 69 is set at a value so that the voltage of the input terminal of the buffer amplifier 59 is brought to zero.

To halt the oscillation of the blade 33, the switches 57 and 63b are turned on to bring the output of the sign-wave generating circuit 56 to zero, and to bring the resistance of the FET 65 to zero, thereby making no input to the output amplifier 61. In case the output voltage of the output amplifier 61 increases for some reason, the output voltage of the smoothing circuit 67 increases, which consequently lowers the resistance of the FET 68, and lowers the input level of the output amplifier 61.

When the frequency is varied through the variable resistor 56b, the blade 33 judders abnormally at a specific frequency due to mechanical resonance. In such a case, the sensor coil 53 electromagnetically detects the amplitude of the judder. The voltage detected thereby is full-wave rectified, followed by smoothing by the smoothing circuit 64 so that the gate voltage of the FET 68 drops. As a result, input to the output amplifier 61 is suppressed, and consequently, the judder is controlled.

Figure 9A:
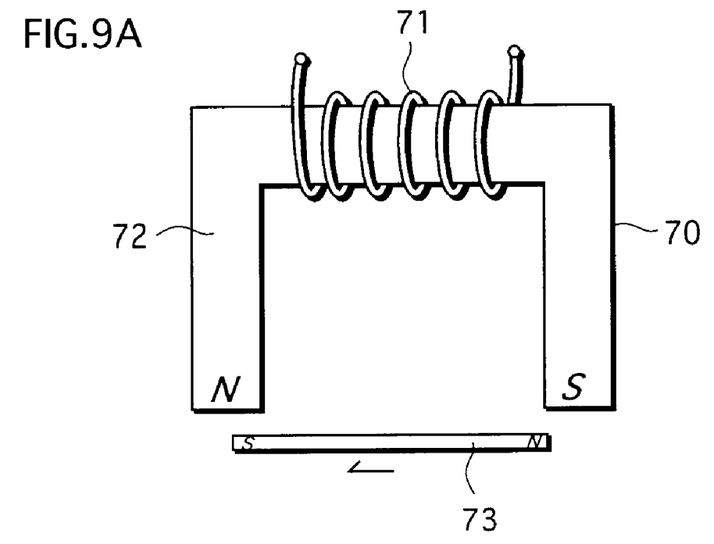
FIG. 9A is view showing the operational principle of a driving mechanism of a microtome according to another embodiment.
Figure 9B:
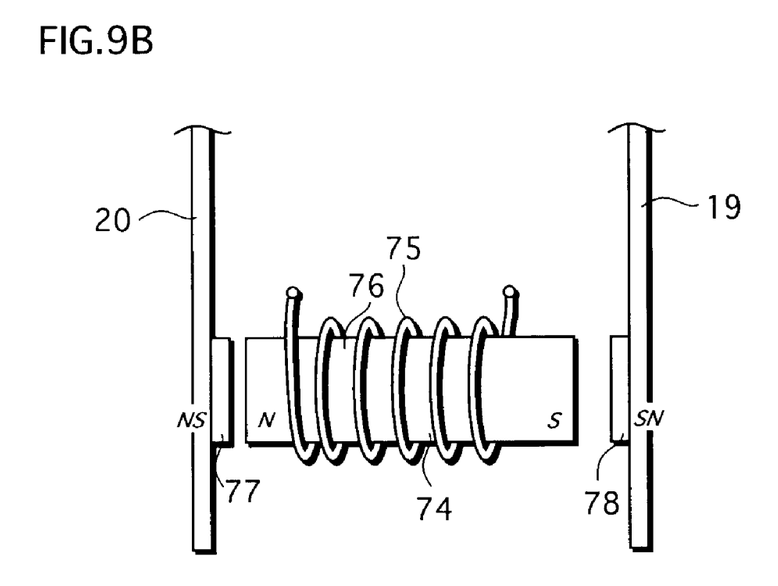
FIG. 9B is a view showing the operational principle of a driving mechanism of a microtome according to yet another embodiment.

Hereinafter, description is given to other embodiments and modifications. One modification of the embodiment shown in FIG. 7 is shown in FIGS. 9A and 9B. As shown in the figures, one alternative to the permanent magnet 47 and the driving electromagnetic 49 may be a permanent magnet 73 and an electromagnet 72 made of an inverted U-shaped core to which a coil 71 is wound around. Another alternative is an electromagnet 76 made of a bar-like core 74 to which a coil 75 is wound around, and a pair of opposing permanent magnets 77 and 78 each arranged to face a respective end of the electromagnet 76. The former modification shown in FIG. 9A is assembled similarly to the embodiment shown in FIG. 4, and the latter modification shown in FIG. 9B is assembled as follows. That is, the electromagnet 76 is fixedly mounted on the base 3, and the permanent magnets 77 and 78 are fixed to the resilient couplers 19 and 20, respectively. The permanent magnet 73 shown in FIG. 9 may be the same one used in the embodiment shown in FIGS. 3 and 4.

Further, the electromagnet 49 shown in FIG. 4 maybe mounted on the movable body 18, and the permanent magnet 47 maybe mounted on the base 3. Still further, the permanent magnet 47 may be an electromagnet.

In the embodiment described above, the base 3 is moved relatively to the table 2. Alternatively, the base 3 is fixed and the table 2 may be constructed to be movable, or any other modification is possible as long as relative movement is made between the table 2 and the base 3. Note that the table 2, the casing 16, and the tray 17 are all fixed directly or indirectly to the main body 1, so that the three components are collectively referred to as a stage. That is to say, the microtome is provided with the stage onto which a specimen is fixedly placed, and with the base that slides relatively to the stage.

Further, in the embodiment described above, the control signal is described as a sign wave. Alternatively, however, a rectangular wave or various other types of signals may be used. Yet, a sign wave is preferable for smooth oscillation.

The above description is focused on a feature of the present invention that the live specimen is used and cut without killing the cells present in the specimen. Yet, it is naturally understood that the microtome of the present invention may be used to slice other types of specimens, such as a specimen solidified with the use of an agent, or a specimen solidified in agar (thus, the cells present in the specimen are no longer alive).

With the construction described above, the present invention achieves the effects as follows. That is, the oscillation of the movable body to which the blade for slicing the specimen is attached is achieved with the use of the driving electromagnet and the permanent magnet (or may be another electromagnet) by supplying the control voltage to the driving electromagnet. With this non-contact construction, the microtome according to the present invention eliminates deterioration in the oscillation that is otherwise caused through a long period of use. In other words, unlike the conventional device, the blade is free from vertical wobbling that may be caused by wearing of the portion of the microtome that is in mechanical contact. Thus, there is no such an occurrence that the specimen is killed by beings mashed by the blade. In addition, the driving mechanism using the electromagnet in combination with the magnet is capable of powerfully oscillating the blade, and thus sharply cutting the specimen.

Further, the resilient couplers supporting the movable body are made out of a plurality of spring plates overlapped in layers. Thus, the resilient couplers allow the blade to oscillate only in the fixed direction.

Still further, the permanent magnet arranged in opposing relation to the electromagnet is magnetized in the thickness direction so that the left half and the right half of the permanent magnet have unlike polarities from each other. This forces the blade to oscillate in a click-like motion, i.e. to oscillate quickly and powerfully, so that the specimen is cut more sharply.

Still further, the presence of feedback circuit serves to suppress the judder that may be caused due to the mechanical resonance at the time of varying the frequency of the control signal. Still further, the amplitude and the frequency of oscillation are varied in a continuous manner. This ensures to achieve optimum slicing depending on the type and the state of the specimen.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. A microtome for cutting a thin slice from a specimen, comprising:

a stage for fixedly placing the specimen thereon;

a base arranged slidably relative to the stage;

a movable body arranged to oscillate in a direction perpendicular to a direction in which the base slides;

a cutting blade for cutting the specimen placed on the stage, the cutting blade being attached to the movable body at a forward part with respect to the sliding direction;

a plurality of resilient couplers coupling the movable body to the base so as to allow for the oscillation;

a first magnet made of an electromagnet and mounted on one of the base and the movable body;

a control circuit for supplying an alternating signal to the first magnet; and a second magnet mounted on the other of the base and the movable body in opposed relation to the first magnet, the second magnet reacting to attraction and repulsion that is alternately resulting from an alternating field generated by the first magnet, so that the movable body is displaced against resilience of the resilient couplers in the direction perpendicular to the sliding direction, whereby the cutting blade oscillates, wherein by sliding the base forward relative to the stage, the cutting blade cuts into the specimen with oscillation so that the thin slice is cut from the specimen.

2. The microtome according to claim 1, wherein the second magnet is different from the first magnet in magnetic pole distance, and the first magnet generates, when energized, magnetic force attracting the second magnet in a direction where unlike polarities are adjacent to each other owing to the different magnetic pole distance.

3. The microtome according to claim 1, wherein the first magnet is fixed to the base, the second magnet is made of a permanent magnet magnetized to have a north pole and a south pole at respective ends thereof, and the permanent magnet is fixed to the movable body with the north pole and the south pole opposing to a pair of legs of a core of the first magnet.

4. The microtome according to claim 1, further comprising an operating unit for variably controlling an amplitude and a frequency of the current passing through the first magnet.

5. The microtome according to claim 1, further comprising a support for supporting the cutting blade, the support being attached to the movable body, wherein the support includes adjusting means for adjusting an angle of the cutting blade relative to the specimen.

6. The microtome according to claim 1, wherein the first magnet is fixed to the base, the second magnet is made of a pair of permanent magnets each magnetized to have a north pole and a south pole in a thickness direction of the permanent magnet, and the pair of permanent magnets are fixed to the movable body with the north pole of one permanent magnet and the south pole of the other magnet opposing to a leg of a core of the first magnet.

7. The microtome according to claim 6, wherein the pair of the permanent magnets are formed into a single piece magnetized in a thickness direction thereof so that a left half and a right half of a facing side of the single piece to the first magnet have unlike magnetic properties.

8. The microtome according to claim 1, further comprising:
- a detector for detecting a magnitude of a current passing through the first magnet; and
- a current control circuit for controlling the current passing through the first magnet so that the detector detects a constant magnitude.

9. The microtome according to claim 8, further comprising an operating unit for variably controlling an amplitude and a frequency of the current passing through the first magnet.

10. The microtome according to claim 1, wherein
- the stage is a tray horizontally supported to store a liquid therein, and
- the specimen is held on the tray in a state being immersed in the liquid, and
- the base slides in the horizontal direction, so that the cutting blade moves forward from its home position to intersect the specimen within the tray.

11. The microtome according to claim 10, further comprising operating means for vertically moving the tray.

12. The microtome according to claim 11, further comprising a dial for setting an amount of the vertical movement of the stage that is to be made for one forwarding movement of the base, whereby a thickness of the slice is set.

13. The microtome according to claim 1, wherein
- the plurality of resilient couplers are arranged in a pair,
- each resilient coupler is made up of a plurality of spring plates overlapped in layers, and
- the pair of resilient couplers is attached to the base with a first end of each resilient coupler being fixed to the base at two separate locations, and a second end of each resilient coupler being fixed to the movable body at lateral sides.

14. The microtome according to claim 13, wherein
- the second magnet is a permanent magnet,
- the second magnet is different from the first magnet in magnetic pole distance, and
- the first magnet generates, when energized, magnetic force attracting the second magnet in a direction where unlike polarities are adjacent to each other owing to the different magnetic pole distance.

15. The microtome according to claim 13, wherein
- the first magnet is fixed to the base,
- the second magnet is made of a permanent magnet magnetized to have a north pole and a south pole at respective ends thereof, and
- the permanent magnet is fixed to the movable body with the north pole and the south pole opposing to a pair of legs of a core of the first magnet.

16. The microtome according to claim 13, wherein
- the first magnet is fixed to the base,
- the second magnet is made of a pair of permanent magnets each magnetized to have a north pole and a south pole in a thickness direction of the permanent magnet, and
- the pair of permanent magnets are fixed to the movable body with the north pole of one permanent magnet and the south pole of the other magnet opposing to a leg of a core of the first magnet.

17. The microtome according to claim 16, wherein
- the pair of the permanent magnets are formed into a single piece magnetized in a thickness direction thereof so that a left half and a right half of a facing side of the single piece to the first magnet have unlike magnetic properties.

* * * * *